(12) United States Patent
Lorant et al.

(10) Patent No.: US 11,382,857 B2
(45) Date of Patent: Jul. 12, 2022

(54) COMPOSITION COMPRISING A FATTY PHASE, A LIPOPHILIC POLYMER AND A VOLATILE HYDROCARBON-BASED OIL

(71) Applicant: L'OREAL, Paris (FR)

(72) Inventors: Raluca Lorant, Chevilly la Rue (FR); Karl Boutelet, Chevilly la Rue (FR); Vincent Grandjon, Chevilly la Rue (FR)

(73) Assignee: L'OREAL, Paris (FR)

( * ) Notice: Subject to any disclaimer, the term of this patent is extended or adjusted under 35 U.S.C. 154(b) by 1 day.

(21) Appl. No.: 16/760,648

(22) PCT Filed: Nov. 15, 2018

(86) PCT No.: PCT/EP2018/081469
§ 371 (c)(1),
(2) Date: Apr. 30, 2020

(87) PCT Pub. No.: WO2019/096954
PCT Pub. Date: May 23, 2019

(65) Prior Publication Data
US 2020/0345621 A1    Nov. 5, 2020

(30) Foreign Application Priority Data

Nov. 15, 2017 (FR) ...................... 1760736

(51) Int. Cl.
| | | |
|---|---|---|
| *A61K 8/31* | (2006.01) | |
| *A61K 8/81* | (2006.01) | |
| *A61Q 5/02* | (2006.01) | |
| *A61Q 5/12* | (2006.01) | |
| *A61Q 15/00* | (2006.01) | |
| *A61Q 17/04* | (2006.01) | |
| *A61Q 19/10* | (2006.01) | |
| *A61K 8/92* | (2006.01) | |
| *A61K 8/06* | (2006.01) | |
| *A61Q 1/06* | (2006.01) | |
| *A61Q 1/04* | (2006.01) | |
| *A61Q 13/00* | (2006.01) | |
| *A61Q 19/00* | (2006.01) | |

(52) U.S. Cl.
CPC ................ *A61K 8/92* (2013.01); *A61K 8/064* (2013.01); *A61K 8/31* (2013.01); *A61K 8/8152* (2013.01); *A61Q 1/06* (2013.01); *A61Q 5/02* (2013.01); *A61Q 5/12* (2013.01); *A61Q 15/00* (2013.01); *A61Q 17/04* (2013.01); *A61Q 19/10* (2013.01); *A61K 2800/48* (2013.01)

(58) Field of Classification Search
None
See application file for complete search history.

(56) References Cited

U.S. PATENT DOCUMENTS

| 4,128,635 A | 12/1978 | Hase et al. | |
|---|---|---|---|
| 2004/0005279 A1* | 1/2004 | Lorant | .................. A61K 8/042 252/588 |
| 2017/0348219 A1* | 12/2017 | Uyama | ................ A61K 8/8152 |

FOREIGN PATENT DOCUMENTS

| EP | 3 235 839 A1 | 10/2017 |
|---|---|---|
| WO | WO 2016/098456 A | 6/2016 |

\* cited by examiner

*Primary Examiner* — Brian Gulledge
(74) *Attorney, Agent, or Firm* — Polsinelli PC

(57) ABSTRACT

The present invention relates to a composition for topical application comprising at least one fatty phase; at least one volatile hydrocarbon-based oil; and at least one lipophilic polymer comprising at least hydroxyethyl acrylate units and acrylate units bearing a lipophilic group, the weight ratio of the sum of all the hydroxyethyl acrylate units to the sum of all the acrylate units bearing a lipophilic group ranging from 1:30 to 1:1 and the lipophilic polymer having a number-average molecular weight Mn ranging from 2000 to 9000 g/mol. The composition in accordance with the invention has improved sensory properties, allowing faster and more complete absorption into the skin. In particular, the composition in accordance with the invention leaves a non-greasy and non-tacky feel on the skin, during and after application, even in the presence of solid fatty substances such as waxes.

21 Claims, No Drawings

COMPOSITION COMPRISING A FATTY PHASE, A LIPOPHILIC POLYMER AND A VOLATILE HYDROCARBON-BASED OIL

CROSS REFERENCE TO RELATED APPLICATIONS

This application is a National Phase filing under 35 U.S.C. § 371 of PCT/EP2018/081469 filed on 15 Nov. 2018; which application in turn claims priority to Application No. 1760736 filed in France on 15 Nov. 2017. The entire contents of each application are hereby incorporated by reference.

The present invention relates to a composition for topical application comprising at least one fatty phase, at least one particular lipophilic polymer and at least one volatile hydrocarbon-based oil, and to the use of said composition in the cosmetic and dermatological fields, in particular for caring for and treating keratin materials.

In the cosmetic field, and more particularly in the field of skincare and photoprotection, it is common practice to use galenical architectures containing a fatty phase structured/thickened with a lipophilic thickener. This makes it possible to improve the efficiency and stability of the products.

In particular, structuring the fatty phase with lipophilic thickeners is particularly advantageous for giving consistency to anhydrous or emulsified compositions intended for caring for or making up the skin. Waxy or pasty fatty substances are very often used to obtain a thickening effect.

However, these types of preparation have the drawback of producing compositions that are greasy on application, which penetrate the skin slowly and incompletely, leaving an unpleasant residual greasy film.

There is thus still a need to make compositions containing a structured fatty phase which do not have these drawbacks and which would be quickly absorbed without leaving a greasy film on the skin.

Moreover, in recent years, the cosmetics market has been marked by a huge demand for formulations containing ingredients of natural origin. Consumers desire formulations that are free of chemicals, to which they prefer ingredients of natural origin, which are renowned for their better tolerance and affinity with the skin, and that are more environmentally friendly.

It is thus sought to obtain care products containing compounds of natural origin which are quite harmless with respect to keratin materials, which have good stability, good microbiological preservation, and which are easy and pleasant to use while nevertheless having the properties required for care products, namely being pleasant to use and not being greasy, tacky or irritant.

The term "natural compound" means a compound that is obtained directly from the earth or the soil, or from plants or animals, via, where appropriate, one or more physical processes, for instance milling, refining, distillation, purification or filtration.

The term "compound of natural origin" means a natural compound that has undergone one or more additional chemical or industrial treatments, giving rise to modifications that do not affect the essential qualities of this compound and/or a compound predominantly comprising natural constituents that may or may not have undergone transformations as indicated above.

As non-limiting examples of additional chemical or industrial treatments bringing about modifications which do not affect the essential qualities of a natural compound, mention may be made of those allowed by the regulatory bodies such as Ecocert (Reference system for cosmetic, biological and ecological products, January 2003), or defined in handbooks recognized in the field, such as *Cosmetics and Toiletries Magazine,* 2005, Vol. 120, 9:10. The Applicant has found, surprisingly, that the combination of a suitably selected lipophilic polymer with a volatile hydrocarbon-based oil in a composition comprising a fatty phase makes it possible to improve the sensory properties of cosmetic compositions containing same, while at the same time allowing faster and more complete absorption into the skin. Thus, one subject of the present invention is a composition for topical application comprising at least one fatty phase; at least one volatile hydrocarbon-based oil; and at least one lipophilic polymer comprising monomer units of formulae (A) and (B):

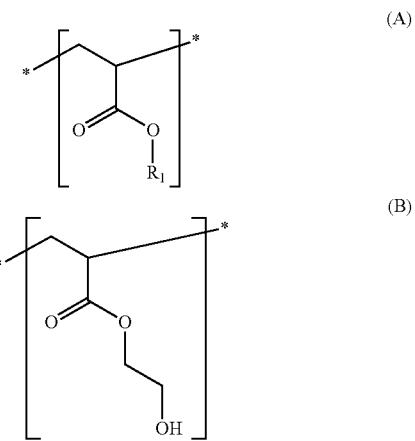

in which:
$R_1$, independently at each occurrence, is chosen from alkyl or alkylene radicals;
with at least 60% by weight of the groups $R_1$ being behenyl radicals, the weight percentage relating to the sum of all the groups $R_1$ present in the polymer;
the weight ratio of the sum of all the hydroxyethyl acrylate units to the sum of all the acrylate units bearing the group $R_1$ ranges from 1:30 to 1:1; and
the sum of all of the units A and B is at least 95% by weight relative to the total weight of the polymer.

The composition in accordance with the invention has improved sensory properties, allowing faster and more complete absorption into the skin. In particular, the composition in accordance with the invention leaves a non-greasy and non-tacky feel on the skin, during and after application, even in the presence of solid fatty substances such as waxes.

Thus, the present invention makes it possible to prepare cosmetic compositions that are nourishing to the skin, containing specific waxy fatty substances and compatible volatile oils, while at the same time having stable, homogeneous textures which are easy to apply and pleasant to use, and which are neither greasy nor tacky nor irritant. This type of product is particularly advantageous for treating dry skin.

Even when the content of lipophilic thickeners and/or the content of fatty phase is high, the compositions according to the invention penetrate rapidly without leaving a greasy film.

The composition in accordance with the invention also has good cosmetic properties approaching those that are usually obtained with silicones, in particular volatile silicones, which makes it possible to limit or even avoid the use of these compounds.

Moreover, the cosmetic composition thus obtained has good stability over time, especially after two months at room temperature and at 45°.

The term "stable composition" refers to a composition which, after 24 hours of storage at any temperatures between 4° C. and 50° C., does not show any macroscopic change in colour, odour or viscosity, or any variation in pH, and shows an absence of grains.

Thus, the composition in accordance with the invention may advantageously be free of emulsifying surfactant conventionally used or may contain a very small content thereof, which enables it to be well tolerated by any skin type, especially fragile skins, and also sensitive skins that are particularly reactive.

A subject of the invention is also a process for the cosmetic treatment of keratin materials, which consists in applying to the keratin materials a composition as defined above.

A subject of the invention is also the use of said composition in cosmetics or dermatology, and in particular for caring for, protecting and/or making up bodily or facial skin, or for haircare.

The composition according to the invention is intended for topical application and thus comprises a physiologically acceptable medium. The term "physiologically acceptable medium" means here a medium that is compatible with keratin materials.

In the context of the present invention, the term "keratin material" especially means the skin, the scalp, keratin fibres such as the eyelashes, the eyebrows, head hair, bodily hair, the nails, and mucous membranes such as the lips, and more particularly the skin (body, face, area around the eyes, eyelids).

In the text hereinbelow, the expression "at least one" is equivalent to "one or more" and, unless otherwise indicated, the limits of a range of values are included in that range.

Fatty Phase

The composition according to the invention comprises at least one fatty phase.

For the purpose of the invention, the fatty phase includes any fatty substance that is liquid at room temperature and atmospheric pressure, generally oils, or that is solid at room temperature and atmospheric pressure, like waxes, or any pasty compound, which is present in said composition.

The fatty phase of the composition in accordance with the invention especially comprises at least one lipophilic polymer as defined previously and at least one volatile hydrocarbon-based oil.

Lipophilic Polymers

The composition in accordance with the invention comprises at least one lipophilic polymer comprising monomer units of formulae (A) and (B):

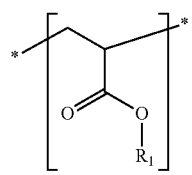

(A)

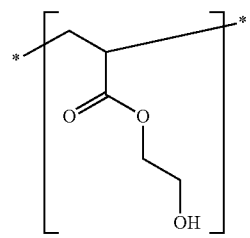

(B)

in which:

$R_1$, independently at each occurrence, is chosen from alkyl or alkylene radicals;

with at least 60% by weight of the groups $R_1$ being behenyl radicals, the weight percentage relating to the sum of all the groups $R_1$ present in the polymer;

the weight ratio of the sum of all the hydroxyethyl acrylate units to the sum of all the acrylate units bearing the group $R_1$ ranges from 1:30 to 1:1; and the sum of all of the units A and B is at least 95% by weight relative to the total weight of the polymer.

Preferably, $R_1$ consists of alkyl radicals, preferably of $C_{16}$-$C_{22}$ alkyl radicals, and more preferentially of behenyl ($C_{22}$) radicals.

Preferably, at least 70% by weight of the groups $R_1$ are behenyl radicals, preferentially at least 80% by weight, and more preferentially at least 90% by weight.

According to a preferred embodiment, all the groups $R_1$ are behenyl radicals.

Preferably, said weight ratio ranges from 1:15 to 1:1, and preferentially ranges from 1:10 to 1:4.

Advantageously, the polymer units present in the polymer consist of the units (A) and (B) previously described.

The polymer has a number-average molecular weight Mn ranging from 2000 to 9000 g/mol, preferably ranging from 5000 to 9000 g/mol. The number-average molecular weight can be measured by the gel permeation chromatography method, for example according to the method described in the example hereinbelow.

Preferably, the polymer has a melting point ranging from 60° C. to 69° C., and preferentially ranging from 63° C. to 67° C. The melting point is measured by differential scanning calorimetry (DSC), for example according to the method described in the example hereinbelow.

The polymer used according to the invention may be prepared by polymerization of the monomer of formula $CH_2$=CH—COO—$R_1$, $R_1$ having the meaning previously described, and of 2-hydroxyethyl acrylate.

The polymerization may be performed according to known methods, such as solution polymerization or emulsion polymerization.

The polymerization is, for example, described in US 2007/0264204.

The lipophilic polymer(s) used in the context of the invention and as described previously may be present in the composition in an amount of active material ranging from 0.1% to 10% by weight, preferably from 0.1% to 3% by weight, relative to the total weight of the composition.

Volatile Hydrocarbon-Based Oils

The composition in accordance with the invention comprises at least one volatile hydrocarbon-based oil.

According to one embodiment of the invention, the volatile hydrocarbon-based oil(s) are different from fragranced oils.

According to another embodiment of the invention, the volatile hydrocarbon-based oil(s) are different from terpenes.

The volatile hydrocarbon-based oil(s) may be chosen from hydrocarbon-based oils containing from 8 to 16 carbon atoms.

The term "hydrocarbon-based oil" means an oil formed essentially from, or even constituted of, carbon and hydrogen atoms, and possibly oxygen, nitrogen, sulfur and/or phosphorus atoms, and containing no silicon or fluorine atoms; it may contain ester, ether, amine or amide groups.

The term "volatile oil" means an oil (or non-aqueous medium) that is capable of evaporating on contact with keratin materials, especially keratin fibre, in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10- to 300 mmHg), preferably ranging from 1.3 Pa to 13 000 Pa (0.01 to 100 mmHg) and preferentially ranging from 1.3 Pa to 1300 Pa (0.01 to 10 mmHg).

The volatile hydrocarbon-based oil(s) may be chosen especially from volatile branched esters, volatile branched alkanes, volatile linear alkanes, and mixtures thereof.

The compositions according to the invention may comprise one or more branched C8-C16 esters, such as isohexyl neopentanoate, isoamyl esters such as isoamyl laurate, or else isononyl isononanoate.

The composition according to the invention may contain one or more volatile branched alkanes. The term "one or more volatile branched alkanes" means, without distinction, "one or more volatile branched alkane oils".

As volatile branched alkanes, mention may be made especially of branched C8-C16 alkanes, such as C8-C16 isoalkanes (also known as isoparaffins), isododecane (also known as 2,2,4,4,6-pentamethylheptane), isodecane, isohexadecane, and for example the oils sold under the trade name Isopar by ExxonMobil or Permethyl® by Presperse.

Preferably, the volatile hydrocarbon-based oil containing from 8 to 16 carbon atoms is chosen from isododecane, isodecane and isohexadecane, and mixtures thereof, and is especially isododecane.

The composition according to the invention may contain one or more volatile linear alkanes. The term "one or more volatile linear alkanes" means, without distinction, "one or more volatile linear alkane oils".

A volatile linear alkane that is suitable for the invention is liquid at room temperature (about 25° C.) and at atmospheric pressure (760 mmHg).

A "volatile linear alkane" that is suitable for the invention refers to a cosmetic linear alkane, which is capable of evaporating on contact with the skin in less than one hour, at room temperature (25° C.) and atmospheric pressure (760 mmHg, i.e. 101 325 Pa), which is liquid at room temperature, in particular having an evaporation rate ranging from 0.01 to 15 mg/cm$^2$/min, at room temperature (25° C.) and atmospheric pressure (760 mmHg).

Preferably, the "volatile linear alkanes" that are suitable for the invention have an evaporation rate ranging from 0.01 to 3.5 mg/cm$^2$/min, at room temperature (25° C.) and atmospheric pressure (760 mmHg).

Preferably, the "volatile linear alkanes" that are suitable for the invention have an evaporation rate ranging from 0.01 to 1.5 mg/cm$^2$/min, at room temperature (25° C.) and atmospheric pressure (760 mmHg).

More preferably, the "volatile linear alkanes" that are suitable for the invention have an evaporation rate ranging from 0.01 to 0.8 mg/cm$^2$/min, at room temperature (25° C.) and atmospheric pressure (760 mmHg).

Even more preferably, the "volatile linear alkanes" that are suitable for the invention have an evaporation rate ranging from 0.01 to 0.3 mg/cm$^2$/min, at room temperature (25° C.) and atmospheric pressure (760 mmHg).

Even more preferably, the "volatile linear alkanes" that are suitable for the invention have an evaporation rate ranging from 0.01 to 0.12 mg/cm$^2$/min, at room temperature (25° C.) and atmospheric pressure (760 mmHg).

The evaporation rate of a volatile alkane in accordance with the invention (and more generally of a volatile solvent) may in particular be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ which is temperature-regulated (25° C.) and hygrometry-regulated (50% relative humidity).

The liquid is allowed to evaporate freely, without stirring it, while providing ventilation by means of a fan (Papst-Motoren, reference 8550 N, rotating at 2700 rpm) placed vertically above the crystallizing dish containing the volatile hydrocarbon-based solvent, the blades being directed towards the crystallizing dish, at a distance of 20 cm relative to the bottom of the crystallizing dish.

The weight of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of the time (in min).

The evaporation rate is then calculated, which corresponds to the tangent to the origin of the curve obtained. The evaporation rates are expressed in mg of volatile solvent evaporated per unit of surface area (cm$^2$) and per unit of time (minutes).

According to one preferred embodiment, the "volatile linear alkanes" that are suitable for the invention have a non-zero vapour pressure (also known as saturation vapour pressure), at room temperature, in particular a vapour pressure ranging from 0.3 Pa to 6000 Pa.

Preferably, the "volatile linear alkanes" that are suitable for the invention have a vapour pressure ranging from 0.3 to 2000 Pa, at room temperature (25° C.).

Preferably, the "volatile linear alkanes" that are suitable for the invention have a vapour pressure ranging from 0.3 to 1000 Pa, at room temperature (25° C.).

More preferably, the "volatile linear alkanes" that are suitable for the invention have a vapour pressure ranging from 0.4 to 600 Pa, at room temperature (25° C.).

Preferably, the "volatile linear alkanes" that are suitable for the invention have a vapour pressure ranging from 1 to 200 Pa, at room temperature (25° C.).

More preferably, the "volatile linear alkanes" that are suitable for the invention have a vapour pressure ranging from 3 to 60 Pa, at room temperature (25° C.).

According to one embodiment, a volatile linear alkane that is suitable for use in the invention may have a flash point that is within the range from 30 to 120° C. and more particularly from 40 to 100° C. The flash point is in particular measured according to standard ISO 3679.

According to one embodiment, an alkane that is suitable for use in the invention may be a volatile linear alkane comprising from 8 to 14 carbon atoms.

According to an advantageous embodiment, the "volatile linear alkanes" that are suitable for use in the invention have an evaporation rate, as defined above, ranging from 0.01 to 3.5 mg/cm$^2$/min, at room temperature (25° C.) and atmospheric pressure (760 mmHg), and comprise from 8 to 14 carbon atoms.

A volatile linear alkane that is suitable for the invention may advantageously be of plant origin.

Such an alkane may be obtained, directly or in several steps, from a plant raw material, such as an oil, a butter, a wax, etc.

As examples of alkanes that are suitable for use in the invention, mention may be made of the alkanes described in patent applications WO 2007/068 371 or WO 2008/155 059 by the company Cognis (mixtures of different alkanes differing by at least one carbon). These alkanes are obtained from fatty alcohols, which are themselves obtained from coconut kernel oil or palm oil.

As examples of linear alkanes that are suitable for use in the invention, mention may be made of n-octane (C8), n-nonane (C9), n-decane (C10), n-undecane (C11), n-dodecane (C12), n-tridecane (C13), n-tetradecane (C14), n-hexadecane (C16) and mixtures thereof. According to a particular embodiment, the volatile linear alkane is chosen from n-nonane, n-undecane, n-dodecane, n-tridecane and n-tetradecane, and mixtures thereof.

The volatile linear alkane may be used alone.

Alternatively or preferentially, a mixture of at least two different volatile linear alkanes, differing from each other by a carbon number n of at least 1, in particular differing from each other by a carbon number of 1 or 2, may be used.

According to a first embodiment, a mixture of at least two different volatile linear alkanes including from 10 to 16 carbon atoms and differing from each other by a carbon number of at least 1 is used. Examples that may especially be mentioned include mixtures of C10/C11, C11/C12 or C12/C13 volatile linear alkanes.

According to another embodiment, a mixture of at least two different volatile linear alkanes including from 10 to 16 carbon atoms and differing from each other by a carbon number of at least 2 is used. Examples that may especially be mentioned include mixtures of C10/C12 or C12/C14 volatile linear alkanes, for an even carbon number n and the C11/C13 mixture for an odd carbon number n.

According to a preferred embodiment, a mixture of at least two different volatile linear alkanes including from 10 to 16 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes including from 8 to 16 carbon atoms and differing from each other by a carbon number of at least 1, also form part of the invention, but mixtures of two volatile linear alkanes according to the invention are preferred (binary mixtures), said two volatile linear alkanes preferably representing more than 95% and better still more than 99% by weight of the total content of volatile linear alkanes in the mixture. According to a particular embodiment of the invention, in a mixture of volatile linear alkanes, the volatile linear alkane having the smallest carbon number is predominant in the mixture.

According to another embodiment of the invention, a mixture of volatile linear alkanes in which the volatile linear alkane having the largest carbon number is predominant in the mixture is used.

As examples of mixtures that are suitable for use in the invention, mention may be made especially of the following mixtures:

from 50% to 90% by weight, preferably from 55% to 80% by weight and more preferentially from 60% to 75% by weight of a Cn volatile linear alkane with n ranging from 8 to 16, from 10% to 50% by weight, preferably from 20% to 45% by weight and preferably from 24% to 40% by weight of a Cn+x volatile linear alkane with x greater than or equal to 1, preferably x=1 or x=2, with n+x between 8 and 16, relative to the total weight of the alkanes in said mixture.

In particular, said mixture of alkanes according to the invention contains:

less than 2% by weight and preferably less than 1% by weight of branched hydrocarbons, and/or less than 2% by weight and preferably less than 1% by weight of aromatic hydrocarbons, and/or less than 2% by weight, preferably less than 1% by weight and preferentially less than 0.1% by weight of unsaturated hydrocarbons in the mixture.

More particularly, a volatile linear alkane that is suitable for use in the invention may be used in the form of an n-undecane/n-tridecane mixture.

In particular, use will be made of a mixture of volatile linear alkanes comprising:

from 55% to 80% by weight and preferably from 60% to 75% by weight of a C11 volatile linear alkane (n-undecane), from 20% to 45% by weight and preferably from 24% to 40% by weight of a C13 volatile linear alkane (n-tridecane), relative to the total weight of the alkanes in said mixture.

According to a particular embodiment, the mixture of alkanes is an n-undecane/n-tridecane mixture. In particular, such a mixture may be obtained according to Example 1 or Example 2 of WO 2008/155 059.

As examples of volatile hydrocarbon-based oils that may be used in context of the invention, mention may be made of:

n-dodecane, such as the product sold under the reference Parafol 12-97 by Sasol;

n-tetradecane, such as the product sold under the reference Parafol 14-97 by Sasol;

a mixture of n-dodecane and n-tetradecane;

isododecane (C12) such as the product sold by the company Ineos;

a mixture of C15-C16 branched alkanes, for example the product sold by the company SEPPIC under the name Emogreen L15;

a mixture of C13-C15 linear and/or branched alkanes, for example the product sold by the company SEPPIC under the name Emosmart L15.

The volatile hydrocarbon-based oil(s) may be present in the composition according to the invention in a content ranging from 0.1% to 90% by weight, preferably ranging from 1% to 70% by weight and preferentially ranging from 3% to 60% by weight, or even from 3% to 40% by weight, relative to the total weight of the composition.

According to a particular embodiment of the invention, the mass ratio between the lipophilic polymer(s) and the volatile hydrocarbon-based oil(s) is between 1:1 and 1:6, preferably between 1:2 and 1:4.

The fatty phase of the composition in accordance with the invention comprises the volatile hydrocarbon-based oil(s) as defined previously. It may also comprise at least one additional volatile or non-volatile oil.

The term "oil" means any fatty substance that is in liquid form at room temperature (25° C.) and at atmospheric pressure.

The additional oil(s) may be non-volatile hydrocarbon-based oils, especially of animal or plant origin, synthetic oils, silicone oils or fluoro oils, or mixtures thereof.

For the purposes of the present invention, the term "silicone oil" means an oil comprising at least one silicon atom, and especially at least one Si—O group.

For the purposes of the present invention, the term "fluoro oil" means an oil comprising at least one fluorine atom.

Non-Volatile Oils

For the purposes of the present invention, the term "non-volatile oil" means an oil with a vapour pressure of less than 0.13 Pa (0.01 mmHg).

The non-volatile oils may be chosen especially from non-volatile hydrocarbon-based oils, or if appropriate fluoro oils and/or silicone oils.

As non-volatile hydrocarbon-based oils that are suitable for implementing the invention, mention may be made especially of:

hydrocarbon-based oils of animal origin, hydrocarbon-based oils of plant origin such as phytostearyl esters, in particular phytostearyl oleate, phytostearyl isostearate and lauroyl/octyl-dodecyl/phytostearyl glutamate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stéarinerie Dubois or those sold under the names Miglyol 810®, 812® and 818® by the company Dynamit Nobel; the refined vegetable perhydrosqualene sold under the name Fitoderm by the company Cognis;

hydrocarbon-based oils of mineral or synthetic origin, for instance:
synthetic ethers containing from 10 to 40 carbon atoms,
linear or branched hydrocarbons of mineral or synthetic origin, such as petroleum jelly, polydecenes, hydrogenated polyisobutene such as Parleam, and squalane, and mixtures thereof, and in particular hydrogenated polyisobutene,
synthetic esters, such as the oils of formula $R_1COOR_2$, in which $R_1$ represents the residue of a linear or branched fatty acid including from 1 to 40 carbon atoms and $R_2$ represents an especially branched hydrocarbon-based chain containing from 1 to 40 carbon atoms, with the proviso that $R_1+R_2$ is ≥10.

The esters may be chosen especially from especially fatty acid esters, for instance:
dicaprylyl carbonate (Cetiol CC from Cognis), cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate,
polyol esters and pentaerythrityl esters, for instance dipentaerythrityl tetrahydroxystearate/tetraisostearate,
esters of diol dimers and of diacid dimers, such as Lusplan DD-DA5® and Lusplan DD-DA7® sold by Nippon Fine Chemical and described in patent application FR 0302809,
alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol,
higher fatty acids such as oleic acid, linoleic acid and linolenic acid, and mixtures thereof, and
dialkyl carbonates, the two alkyl chains possibly being identical or different, such as the dicaprylyl carbonate sold under the name Cetiol CC® by Cognis,
non-volatile silicone oils, for instance non-volatile polydimethylsiloxanes (PDMSs), polydimethylsiloxanes comprising alkyl or alkoxy groups that are on the side and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof,
and mixtures thereof.

Additional Volatile Oils

The additional oil(s) may be volatile oils other than the volatile hydrocarbon-based oils as defined above.

Additional volatile oils that may be used include volatile silicones, for instance volatile linear or cyclic silicone oils, especially those having a viscosity ≤8 centistokes ($8\times10^{-6}$ m$^2$/s), and especially containing from 2 to 10 silicon atoms and in particular from 2 to 7 silicon atoms, these silicones optionally including alkyl or alkoxy groups containing from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof. Volatile fluoro oils such as nonafluoromethoxybutane or perfluoromethylcyclopentane, and mixtures thereof, may also be used.

It is also possible to use a mixture of the oils mentioned above.

The fatty phase of the composition in accordance with the invention may also comprise one or more pasty fatty substances.

For the purposes of the present invention, the term "pasty fatty substance" means a lipophilic fatty compound that undergoes a reversible solid/liquid change in state, which has, in the solid state, an anisotropic crystal organization and which includes, at a temperature of 23° C., a liquid fraction and a solid fraction.

In other words, the starting melting point of the pasty fatty substance may be less than 23° C. The liquid fraction of the pasty fatty substance measured at 23° C. may represent 9% to 97% by weight of the pasty fatty substance. This fraction that is liquid at 23° C. preferably represents between 15 and 85% and more preferably between 40 and 85% by weight. For the purposes of the invention, the melting point corresponds to the temperature of the most endothermic peak observed on thermal analysis (DSC) as described in standard ISO 11357-3; 1999. The melting point of a pasty fatty substance may be measured using a differential scanning calorimeter (DSC), for example the calorimeter sold under the name MDSC 2920 by the company TA Instruments.

The measuring protocol is as follows:

A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the heat of fusion consumed at 23° C. to the heat of fusion of the pasty fatty substance. The heat of fusion of the pasty fatty substance is the heat consumed by the substance in order to pass from the solid state to the liquid state. The pasty fatty substance is said to be in the solid state when all of its mass is in crystalline solid form. The pasty fatty substance is said to be in the liquid state when all of its mass is in liquid form.

The heat of fusion of the pasty fatty substance is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3:1999.

The heat of fusion of the pasty fatty substance is the amount of energy required to make the pasty fatty substance change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty fatty substance measured at 32° C. preferably represents from 30% to 100% by weight of the pasty fatty substance, preferably from 50% to 100%, more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C. The liquid fraction of the pasty fatty substance measured at 32° C. is equal to the ratio of the heat of fusion consumed at 32° C. to the heat of fusion of the pasty fatty substance. The heat of fusion consumed at 32° C. is calculated in the same way as the heat of fusion consumed at 23° C.

The pasty fatty substance is preferably chosen from synthetic fatty substances and fatty substances of plant origin. A pasty fatty substance may be obtained by synthesis from starting materials of plant origin.

The pasty fatty substance is advantageously chosen from:
lanolin and derivatives thereof,
polyol ethers chosen from pentaerythrityl ethers of polyalkylene glycol, fatty alkyl ethers of sugar, and mixtures thereof, the pentaerythrityl ether of polyethylene glycol including 5 oxyethylene units (5 OE) (CTFA name: PEG-5 Pentaerythrityl Ether), the polypropylene glycol pentaerythrityl ether including 5 oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil,
polymeric or non-polymeric silicone compounds,
polymeric or non-polymeric fluoro compounds,
vinyl polymers, especially:
olefin homopolymers and copolymers,
hydrogenated diene homopolymers and copolymers,
liposoluble polyethers resulting from polyetherification between one or more C2-C100 and preferably C2-C50 diols,
esters,
and/or mixtures thereof.

The pasty fatty substance is preferably a polymer, especially a hydrocarbon-based polymer.

Liposoluble polyethers that are particularly preferred are copolymers of ethylene oxide and/or of propylene oxide with C6-C30 long-chain alkylene oxides, more preferably such that the weight ratio of the ethylene oxide and/or of the propylene oxide to the alkylene oxides in the copolymer is from 5:95 to 70:30. In this family, mention will be made especially of copolymers such as long-chain alkylene oxides arranged in blocks with an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, especially such as the product sold under the brand name Softisan 649 by the company Sasol,
the arachidyl propionate sold under the brand name Waxenol 801 by Alzo, phytosterol esters,
fatty acid triglycerides and derivatives thereof,
pentaerythrityl esters,
esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl isostearyl dimer dilinoleate (Lusplan PI-DA, Lusplan PHY/IS-DA), phytosteryl/isosteryl/cetyl/stearyl/behenyl dimer dilinoleate (Plandool H or Plandool S), and mixtures thereof,
mango butter, such as the product sold under the reference Lipex 203 by the company AarhusKarlshamn,
hydrogenated soybean oil, hydrogenated coconut kernel oil, hydrogenated rapeseed oil, mixtures of hydrogenated vegetable oils such as the mixture of hydrogenated soybean, coconut kernel, palm and rapeseed vegetable oil, for example the mixture sold under the reference Akogel® by the company AarhusKarlshamn (INCI name: Hydrogenated Vegetable Oil),
shea butter, in particular the product whose INCI name is *Butyrospermum parkii* Butter, such as the product sold under the reference Sheasoft by the company AarhusKarlshamn,
cocoa butter, in particular the product which is sold under the name CT Cocoa Butter Deodorized by the company Dutch Cocoa BV or the product which is sold under the name Beurre De Cacao NCB HD703 758 by the company Barry Callebaut,
shorea butter, in particular the product which is sold under the name Dub Shorea T by the company Stéarinerie Dubois,
and mixtures thereof.

According to a preferred embodiment, the pasty fatty substance is chosen from shea butter, cocoa butter, shorea butter, a mixture of hydrogenated soybean, coconut kernel, palm and rapeseed vegetable oils, and mixtures thereof, and more particularly those referenced above.

The fatty phase of the composition in accordance with the invention may also comprise at least one wax.

The waxes under consideration in the context of the present invention are generally lipophilic compounds that are solid and deformable or undeformable at room temperature (25° C.), with a solid/liquid reversible change of state, having a melting point of greater than or equal to 30° C., which may range up to 200° C. and especially up to 120° C.

By bringing one or more waxes, in accordance with the invention, to the liquid state (melting), it is possible to render them miscible with one or more oils and to form a macroscopically homogeneous wax(es)+oil(s) mixture, but on returning the temperature of said mixture to room temperature, recrystallization of the wax(es) in the oil(s) of the mixture is obtained.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The measuring protocol is as follows:
A sample of 5 mg of wax placed in a crucible is subjected to a first temperature rise ranging from −20° C. to 100° C., at a heating rate of 10° C./minute, then is cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in a composition according to the invention are chosen from waxes that are solid at room temperature, of animal, plant, mineral or synthetic origin, and mixtures thereof. They may be hydrocarbon-based, fluoro and/or silicone waxes.

Examples that may especially be mentioned include hydrocarbon-based waxes, such as natural beeswax (or bleached beeswax), synthetic beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 and 3080 sold by the company Nippon Seiro, ceresins or ozokerites, for instance isoparaffins of which the melting point is below 40° C., such as the product EMW-0003 sold by the company Nippon Seiro, α-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes, the sunflower seed wax sold by the company Koster Keunen under the reference sunflower wax.

Mention may also be made of silicone waxes, for instance alkyl or alkoxy dimethicones containing from 16 to 45 carbon atoms, and fluoro waxes.

According to a particular embodiment, the wax used in a composition in accordance with the invention has a melting point of greater than 35° C., better still greater than 40° C., or even greater than 45° C. or greater than 55° C.

According to a preferred embodiment, the wax(es) are chosen from polymethylene waxes; the silicone wax sold under the name Dow Corning 2501 Cosmetic Wax by the company Dow Corning (INCI name: bis-PEG-18 methyl ether dimethyl silane); beeswax; plant waxes, such as carnauba wax; the mixture of polyglycerolated (3 mol) vegetable (mimosa/jojoba/sunflower) waxes sold under the name Hydracire S by the company Gattefosse, the hydrogenated castor oil sold under the name Antisettle CVP by the company Cray Valley.

The other fatty substances that may be present in the fatty phase are, for example, fatty acids including from 8 to 30 carbon atoms, for instance stearic acid, lauric acid or palmitic acid; fatty alcohols including from 8 to 30 carbon atoms, for instance stearyl alcohol or cetyl alcohol and mixtures thereof (cetearyl alcohol).

The fatty phase may also contain other compounds dissolved in the oils, such as gelling agents and/or structuring agents.

These compounds may be chosen especially from gums, such as silicone gums (dimethiconol); silicone resins, such as trifluoromethyl (C1-C4)alkyl dimethicone and trifluoropropyl dimethicone, and silicone elastomers, for instance the products sold under the KSG names by the company Shin- Etsu, under the name Trefil by the company Dow Corning or under the Gransil names by the company Grant Industries; and mixtures thereof.

These fatty substances may be chosen in a varied manner by a person skilled in the art in order to prepare a composition having the desired properties, for example in terms of consistency or texture.

According to a particular embodiment of the invention, the composition comprises at least one solid fatty substance, in particular a wax.

According to a particular embodiment of the invention, the composition comprises less than 5% by weight of silicone compound such as silicone fatty substances, and in particular silicone oils, especially less than 2% by weight, or even less than 1% by weight, even better still less than 0.5% by weight, relative to the total weight of the composition. Preferably, the composition is free of silicone compound.

The composition according to the invention may be in various presentation forms conventionally used for topical application and especially in the form of dispersions of the serum type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, or vesicular dispersions of ionic and/or nonionic type. These compositions are prepared according to the usual methods. In addition, the compositions used according to the invention may be more or less fluid and may have the appearance of a gel, a white or coloured cream, an ointment, a milk, a serum, a paste or a foam.

According to a particular embodiment, the composition according to the invention is in the form of an anhydrous composition.

For the purposes of the present invention, the term "anhydrous" refers to a composition comprising a content of less than or equal to 1% by weight and preferably less than or equal to 0.5% by weight of water relative to the total weight of said composition, or which is even free of water. Where appropriate, such small amounts of water may especially be introduced by ingredients of the composition that may contain residual amounts thereof.

According to another particular embodiment, the composition according to the invention is in the form of a water-in-oil emulsion comprising a continuous oily phase and an aqueous phase dispersed in said oily phase, or in the form of an oil-in-water emulsion comprising a continuous aqueous phase and an oily phase dispersed in said aqueous phase.

When the composition is in the form of an anhydrous composition, the proportion of the fatty phase may range, for example, from 30% to 99% by weight and preferably from 50% to 90% by weight relative to the total weight of the composition.

When the composition is in the form of an emulsion, the proportion of the fatty phase may range, for example, from 1% to 80% by weight and preferably from 5% to 40% by weight relative to the total weight of the composition.

These indicated amounts do not comprise the content of lipophilic surfactants.

Aqueous Phase

When the composition in accordance with the invention is in the form of an emulsion, the aqueous phase comprises at least water. Depending on the presentation form of the composition, the amount of aqueous phase may range from 0.1% to 99% by weight, preferably from 0.5% to 98% by weight, better still from 30% to 95% by weight and even better still from 40% to 95% by weight relative to the total weight of the composition. This amount depends on the presentation form of the desired composition. The amount of water may represent all or some of the aqueous phase and it is generally at least 30% by weight relative to the total weight of the composition, preferably at least 50% by weight, better still at least 60% by weight.

The aqueous phase may comprise at least one hydrophilic solvent, for instance substantially linear or branched lower monoalcohols containing from 1 to 8 carbon atoms, such as ethanol, propanol, butanol, isopropanol or isobutanol; polyols, such as propylene glycol, isoprene glycol, butylene glycol, glycerol, sorbitol, polyethylene glycols and derivatives thereof; and mixtures thereof.

The emulsions in accordance with the invention may comprise at least one emulsifier chosen from amphoteric, anionic, cationic and nonionic emulsifiers, used alone or as a mixture. The emulsifiers are chosen in an appropriate manner according to the emulsion to be obtained (W/O or O/W emulsion).

The emulsifiers are generally present in the composition in an active material proportion ranging from 0.1% to 30% by weight and preferably from 0.2% to 20% by weight relative to the total weight of the composition.

For the W/O emulsions, examples of emulsifiers that may be mentioned include dimethicone copolyols such as the mixture of cyclomethicone and of dimethicone copolyol sold under the name DC 5225 C by the company Dow Corning, the oxyethylenated polydimethylsiloxane PEG-10 Dimethicone sold under the name KF 60117 by the company Shin-Etsu, alkyl dimethicone copolyols such as the laurylmethicone copolyol sold under the name Dow Corning 5200 Formulation Aid by the company Dow Corning and the cetyl dimethicone copolyol sold under the name Abil EM 90@ by the company Goldschmidt, or the mixture polyglyceryl-4 isostearate/cetyl dimethicone copolyol/hexyl laurate sold under the name Abil WE 09 by the company Goldschmidt. One or more co-emulsifiers may also be added thereto. The co-emulsifier may be advantageously chosen from the group comprising polyol alkyl esters. Polyol alkyl esters that may especially be mentioned include glycerol and/or sorbitan esters, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

Examples of emulsifiers that may be mentioned for the O/W emulsions include nonionic surfactants, and especially esters of polyols and of fatty acids with a saturated or unsaturated chain including, for example, from 8 to 24 carbon atoms and better still from 12 to 22 carbon atoms, and the oxyalkylenated derivatives thereof, i.e. derivatives including oxyethylene and/or oxypropylene units, such as glyceryl esters of $C_8$-$C_{24}$ fatty acids, and the oxyalkylenated derivatives thereof; polyethylene glycol esters of $C_8$-$C_{24}$ fatty acids, sorbitol esters of $C_8$-$C_{24}$ fatty acids, and the oxyalkylenated derivatives thereof; fatty alcohol ethers; sugar ethers of $C_8$-$C_{24}$ fatty alcohols, and mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate) and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Examples of fatty alcohol ethers that may be mentioned include polyethylene glycol ethers of fatty alcohols including from 8 to 30 carbon atoms and in particular from 10 to 22 carbon atoms, such as polyethylene glycol ethers of cetyl alcohol, of stearyl alcohol or of cetearyl alcohol (mixture of cetyl alcohol and stearyl alcohol). Mention may be made, for example, of ethers including from 1 to 200 and preferably from 2 to 100 oxyethylene groups, such as those with the CTFA name Ceteareth-20 or Ceteareth-30, and mixtures thereof.

Examples of sugar mono- or polyalkyl esters or ethers that may be mentioned include the methylglucose isostearate sold under the name Isolan-IS by the company Degussa Goldschmidt, or else the sucrose distearate sold under the name Crodesta F50 by the company Croda, and the sucrose stearate sold under the name Ryoto sugar ester S 1570 by the company Mitsubishi Kagaku Foods.

Mention may also be made of lipoamino acids and salts thereof, such as monosodium and disodium acylglutamates, for instance monosodium stearoyl glutamate, sold under the name Amisoft HS-11PF, and disodium stearoyl glutamate, sold under the name Amisoft HS-21P, by Ajinomoto.

According to a particular embodiment of the invention, the composition comprises less than 5% by weight of emulsifying surfactant, in particular less than 2% by weight, or even less than 1% by weight, even better still less than 0.5% by weight, relative to the total weight of the composition. Preferably, the composition is free of emulsifying surfactant.

In a known manner, all the compositions of the invention may comprise one or more of the adjuvants that are common in cosmetics and dermatology: hydrophilic or lipophilic gelling agents and/or thickeners; moisturizers; emollients; hydrophilic or lipophilic active agents; free-radical scavengers; sequestrants; antioxidants; preserving agents; basifying or acidifying agents; fragrances; film-forming agents; fillers; and mixtures thereof.

The amounts of these various adjuvants are those conventionally used in the fields under consideration. In particular, the amounts of active agents vary according to the desired aim and are those conventionally used in the fields under consideration, for example from 0.1% to 20% and preferably from 0.5% to 10% by weight relative to the total weight of the composition.

Active Agents

Non-limiting examples of active agents that may be mentioned include ascorbic acid and derivatives thereof such as 5,6-di-O-dimethylsilyl ascorbate (sold by the company Exsymol under the reference PRO-AA), the potassium salt of dl-alpha-tocopheryl-21-ascorbyl phosphate (sold by the company Senju Pharmaceutical under the reference Sepivital EPC), magnesium ascorbyl phosphate, sodium ascorbyl phosphate (sold by the company Roche under the reference Stay-C 50); phloroglucinol; enzymes; and mixtures thereof. According to a preferred embodiment of the invention, use is made, among oxidation-sensitive hydrophilic active agents, of ascorbic acid. The ascorbic acid may be of any nature. Thus, it may be of natural origin in powder form or in the form of orange juice, preferably orange juice concentrate. It may also be of synthetic origin, preferably in powder form.

As other active agents that can be used in the composition of the invention, examples that may be mentioned include moisturizers, such as protein hydrolysates and polyols, for instance glycerol, glycols, for instance polyethylene glycols; natural extracts; anti-inflammatory agents; oligomeric proanthocyanidins; vitamins such as vitamin A (retinol), vitamin E (tocopherol), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; algal, fungal, plant, yeast or bacterial extracts; steroids; antibacterial active agents, such as 2,4,4'-trichloro-2'-hydroxydiphenyl ether (or triclosan), 3,4,4'-trichlorocarbanilide (or triclocarban) and the acids indicated above, and in particular salicylic acid and derivatives thereof; matt-effect agents, for instance fibres; tensioning agents; UV-screening agents, in particular organic UV-screening agents; and mixtures thereof.

Needless to say, a person skilled in the art will take care to select the optional adjuvant(s) added to the composition according to the invention such that the advantageous properties intrinsically associated with the composition in accordance with the invention are not, or are not substantially, adversely affected by the envisioned addition.

The examples that follow will allow the invention to be understood more clearly, without, however, being limiting in nature. The amounts indicated are weight percentages of starting material, unless otherwise mentioned. The compound names are given as the chemical names or the INCI names.

EXAMPLES

Example of Synthesis of the Lipophilic Polymer

Determination of the molecular weight by gel permeation chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes to aid dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 μm nylon filter, before being injected into the liquid chromatograph. The standards used for the calibration are the Easi Vial narrow polystyrene (PS) standards from Agilent Technologies.

Polystyrene standards ranging from 2 520 000 to 162 daltons were used for the calibration.

The system is equipped with a PSS SECcurity 1260 RI detector. The polystyrene calibration curve was used to determine the average molecular weight. The recording of the diagrams and the determination of the various molecular weights were performed by the Win GPC Unichrom 81 program.

Determination of the melting point by differential scanning calorimetry (or DSC):

This method describes the general procedure for determining the melting point of polymers by differential scanning calorimetry. This method is based on the standards ASTM E791 and ASTM D 34182 and the DSC calibration is performed according to standard ASTM E 9672.

Behenyl Acrylate/2-Hydroxyethyl Acrylate Copolymer (Polymer 1):

175 g of behenyl acrylate, 25 g of 2-hydroxyethyl acrylate and 0.4 g of 2,2'-azobis(2-methylbutyronitrile) (Akzo Nobel) were added with stirring over 60 minutes at 80° C., to 40 g of isopropanol in a 4-necked flask equipped with side-blade mixer, an internal thermometer, two funnels, a reflux condenser, and an extension for two other necks, after having removed the oxygen from the system by means of a nitrogen flush for 20 minutes. The mixture was stirred at 80° C. for 3 hours. The solvent was then removed by vacuum distillation, 1 g of dilauryl peroxide was then added and the reaction was continued for 60 minutes at 110° C. The step was repeated. The mixture was then cooled to 90° C., a stream of demineralized water was added and the mixture was then stirred. The water was removed by vacuum distillation.

Molecular weight: $M_n$=7300 g/mol, $M_w$=21 000, $M_w/M_n$=2.8

Melting point: 65° C.

Formulation Examples

The rate of absorption of the composition into the skin is evaluated by a panel of eight experts trained in the description of care products. The sensory evaluation is performed as follows: 0.05 ml of product is applied to the back of the hand and the time required for total penetration of the product is evaluated.

The rate of absorption is noted on a scale with four levels: very slow, moderate, rapid, very rapid.

Comparative Examples 1

The following compositions were prepared.

|   |   | A (invention) | B (invention) | C (invention) |
|---|---|---|---|---|
| A | Dodecane (Parafol 12-97 from Sasol) | 10.00 | — | — |
|   | Undecane/tridecane (Cetiol UT from BASF) | — | 10.00 | — |
|   | Isododecane (Isododecane from Ineos) | — | — | 10.00 |
|   | Polymer 1 as previously synthesized | 4.00 | 4.00 | 4.00 |
|   | Diisopropyl sebacate (DUB DIS from Stearinerie Dubois) | 5.00 | 5.00 | 5.00 |
| B | Xanthan gum | 0.10 | 0.10 | 0.10 |
| C | Preserving agent(s) | 0.20 | 0.20 | 0.20 |
|   | Glycerol | 8.00 | 8.00 | 8.00 |
|   | Acrylates copolymer (Carbopol Aqua SF-1 Polymer from Lubrizol) | 1.00 | 1.00 | 1.00 |
|   | Water | 71.45 | 71.45 | 71.45 |
| D | Triethanolamine | 0.25 | 0.25 | 0.25 |

|   |   | D (outside the invention) | E (outside the invention) | F (outside the invention) |
|---|---|---|---|---|
| A | Dodecane (Parafol 12-97 from Sasol) | — | 10.00 | — |
|   | Cyclohexasiloxane (Xiameter PMX-0246 Cyclohexasiloxane from Dow Corning) | 10.00 | — | — |
|   | Mineral oil (Marcol 82 from ExxonMobil Chemical) | — | — | 10.00 |
|   | Polymer 1 as previously synthesized | 4.00 | — | 4.00 |
|   | Poly C10-30 alkyl acrylate (Intelimer IPA 13-6 Polymer from Evonik Materials Netherlands B.V.) | — | 4.00 | — |
|   | Diisopropyl sebacate | 5.00 | 5.00 | 5.00 |
| B | Xanthan gum | 0.10 | 0.10 | 0.10 |
| C | Preserving agent(s) | 0.20 | 0.20 | 0.20 |
|   | Glycerol | 8.00 | 8.00 | 8.00 |
|   | Acrylates copolymer (Carbopol Aqua SF-1 Polymer from Lubrizol) | 1.00 | 1.00 | 1.00 |
|   | Water | 71.45 | 71.45 | 71.45 |
| D | Triethanolamine | 0.25 | 0.25 | 0.25 |

Procedure:

The constituents of phase A are weighed out in a beaker, and the whole is then heated at 80° C. on a water bath.

The constituents of phase C are weighed out in a second beaker, and the xanthan gum (phase B) is then sprinkled in as a fine rain with stirring using a deflocculator (such as a Rayneri blender) until a homogeneous mixture is obtained; the whole is heated at 80° C. The constituents of phase C are incorporated into phase A with stirring using an emulsifying machine of rotor-stator type (such as a Rayneri blender) at a speed of 3000 rpm and cooling of the whole is commenced. At 50° C., phase D is added, and the stirring is then reduced to 2500 rpm. Cooling is continued with stirring down to 18-20° C. A fluid white emulsion is obtained.

The compositions thus obtained are evaluated after 24 hours at room temperature.

Observations:

Compositions A, B and C combining a lipophilic polymer as claimed (Polymer 1) with a volatile hydrocarbon (compositions in accordance with the invention) are in the form of homogeneous emulsions, without any grain perceived during their application, which leave no greasy film, are easy to apply and are very rapidly absorbed by the skin.

Composition D combining a lipophilic polymer as claimed (Polymer 1) with a volatile silicone oil (comparative composition) is not stable, is sparingly homogeneous and has macroscopic grains, which is a sign of instability/incompatibility between the volatile oil and the lipophilic polymer.

For composition E combining a lipophilic polymer not forming part of the invention (Intelimer IPA 13-6 Polymer from Evonik Materials Netherlands B.V.) with a volatile hydrocarbon (comparative composition), the emulsion cannot be prepared, substantial macroscopic crystallization is observed; the test is not homogeneous and is not cosmetically acceptable, the composition contains numerous grains.

Composition F combining a polymer as claimed (Polymer 1) with a non-volatile mineral oil (comparative composition) is in the form of a homogeneous emulsion. However, on application to the skin, the composition leaves a greasy film, it is not easy to apply and it is only absorbed very slowly by the skin.

Comparative Examples 2

The following compositions were prepared.

|   |   | G (invention) | H (outside the invention) |
|---|---|---|---|
| A | Isohexadecane (Isohexadecane from Ineos) | 10.00 | — |
|   | Isoeicosane (Isoeicosane from Ineos) | — | 10.00 |
|   | Polymer 1 as previously synthesized | 4.00 | 4.00 |
|   | Diisopropyl sebacate (DUB DIS from Stéarinerie Dubois) | 5.00 | 5.00 |
| B | Xanthan gum | 0.10 | 0.10 |
| C | Preserving agent(s) | 0.10 | 0.10 |
|   | Glycerol | 8.00 | 8.00 |
|   | Caprylyl glycol | 0.1 | 0.1 |
|   | Acrylates copolymer (Carbopol Aqua SF-1 Polymer from Lubrizol) | 1.00 | 1.00 |
|   | Water | 71.45 | 71.45 |
| D | Triethanolamine | 0.25 | 0.25 |

Procedure:

The constituents of phase A are weighed out in a beaker, and the whole is then heated at 80° C. on a water bath.

The constituents of phase C are weighed out in a second beaker, and the xanthan gum (phase B) is then sprinkled in as a fine rain with stirring using a deflocculator (such as a Rayneri blender) until a homogeneous mixture is obtained; the whole is heated at 80° C. The constituents of phase C are incorporated into phase A with stirring using an emulsifying machine of rotor-stator type (such as a Rayneri blender) at a speed of 3000 rpm and cooling of the whole is commenced. At 50° C., phase D is added, and the stirring is then reduced to 2500 rpm. Cooling is continued with stirring down to 18-20° C. A fluid white emulsion is obtained.

The compositions thus obtained are evaluated after 24 hours at room temperature.

Observations:

Composition G combining a lipophilic polymer as claimed (Polymer 1) and a volatile hydrocarbon (composition in accordance with the invention) is in the form of a homogeneous emulsion, without any grain perceived during its application, which leaves no greasy film, is easy to apply and is rapidly absorbed by the skin.

Composition H combining a polymer as claimed (Polymer 1) and a non-volatile hydrocarbon (comparative composition) is in the form of a homogeneous emulsion. However, on application to the skin, the composition leaves a greasy film, it is not easy to apply and it is only absorbed very slowly by the skin.

Comparative Examples 3

The following compositions were prepared.

|   |   | I (invention) | J (outside the invention) |
|---|---|---|---|
| A | Isohexadecane (Isohexadecane from Ineos) | 10.00 | 10.00 |
|   | Polymer 1 as previously synthesized | 4.00 | — |
|   | Poly C10-30 alkyl acrylate (Intelimer IPA 13-6 Polymer from Evonik Materials Netherlands B.V.) | — | 4.00 |
|   | Diisopropyl sebacate (DUB DIS from Stearinerie Dubois) | 5.00 | 5.00 |
| B | Xanthan gum | 0.10 | 0.10 |
| C | Preserving agent(s) | 0.20 | 0.20 |
|   | Glycerol | 8.00 | 8.00 |
|   | Acrylates copolymer (Carbopol Aqua SF-1 Polymer from Lubrizol) | 1.00 | 1.00 |
|   | Water | 71.45 | 71.45 |
| D | Triethanolamine | 0.25 | 0.25 |

Procedure:

The constituents of phase A are weighed out in a beaker, and the whole is then heated at 80° C. on a water bath.

The constituents of phase C are weighed out in a second beaker, and the xanthan gum (phase B) is then sprinkled in as a fine rain with stirring using a deflocculator (such as a Rayneri blender) until a homogeneous mixture is obtained; the whole is heated at 80° C. The constituents of phase C are incorporated into phase A with stirring using an emulsifying machine of rotor-stator type (such as a Rayneri blender) at a speed of 3000 rpm and cooling of the whole is commenced. At 50° C., phase D is added, and the stirring is then reduced to 2500 rpm. Cooling is continued with stirring down to 18-20° C. A fluid white emulsion is obtained.

The compositions thus obtained are evaluated after 24 hours at room temperature.

Observations:

Composition I combining a lipophilic polymer as claimed (Polymer 1) with a volatile hydrocarbon (compositions in accordance with the invention) are in the form of homogeneous emulsions, without any grain perceived during their application, which leave no greasy film, are easy to apply and are very rapidly absorbed by the skin.

For composition J combining a lipophilic polymer not forming part of the invention (Intelimer IPA 13-6 Polymer from Evonik Materials Netherlands B.V.) with a volatile hydrocarbon (comparative composition), the emulsion cannot be prepared, substantial macroscopic crystallization is observed; the test is not homogeneous and is not cosmetically acceptable, the composition contains numerous grains.

Illustrative Examples

| Lipstick | K |
|---|---|
| Polymer 1 as previously synthesized | 20% |
| Pigment(s) | qs |
| Hydrogenated isoparaffin | 16.2% |
| (6-8 mol of isobutylene) | |
| (Parleam from NOF Corporation) | |
| Isododecane | 30% |
| (Permethyl 99 A from Permethyl) | |
| Phenyltrimethylsiloxytrisiloxane, | 16% |
| viscosity 20 cSt, PM 372 (Dow Corning | |
| 556 Cosmetic Grade Fluid from Dow Corning) | |
| Polyhydroxystearic acid | 2% |
| (Dispersun DSP OL-300 from | |
| Innospec Active Chemicals) | |
| Stabilized liquid lanolin | 3% |
| (Lanogene LP 308 from Amerchol) | |
| Demineralized water | 0.3% |
| Pentylene glycol | 2% |
| (616751 Hydrolite-5 from Symrise) | |

| Body and hair shower gel | L |
|---|---|
| Sodium lauryl ether sulfate | 15% |
| (2.0 or 2.2 EO) as an aqueous | |
| 70% solution (Texapon AOS | |
| 225 UP from BASF) | |
| Polymer 1 as | 1% |
| previously synthesized | |
| Refined sunflower oil | 3% |
| Dodecane | 1% |
| (Parafol 12-97 from Sasol) | |
| Cocoylamidopropylbetaine | 12% |
| as an aqueous 38% solution (Dehyton | |
| PK 45 from BASF) | |
| Hydroxypropyl guar trimethylammonium | 0.2% |
| chloride (Jaguar C-13-S from Rhodia) | |
| Slightly crosslinked acrylic | 4% |
| polymer as an emulsion (Carbopol | |
| Aqua SF-1 Polymer from Lubrizol) | |
| Fragrance(s) | qs |
| Demineralized water | qs 100 |

| O/W Antisun milk | M |
|---|---|
| Glycerol | 5% |
| Demineralized water | qs 100 |
| Polymer 1 as | 4% |
| previously synthesized | |
| Undecane/tridecane | 3% |
| (Cetiol UT from BASF) | |
| Crosslinked acrylic | 0.4% |
| acid/alkyl acrylate polymer | |
| (Pemulen TR-2 Polymer from Lubrizol) | |
| C12-15 Alkyl benzoate | 10% |
| (Tegosoft TNS from Evonik Goldschmidt) | |
| Glyceryl mono/distearate/ | 3% |
| polyethylene (100 EO) glycol stearate mixture | |
| (Arlacel 165-FL-(CQ) from Croda) | |
| UV-screening agent(s) | 20% |

| Deodorant cream | N |
|---|---|
| Stearyl alcohol | 25% |
| Hydrogenated castor oil | 3% |
| (Cutina HR Powder from BASF) | |
| Tetradecane | 5% |
| (Parafol 14-97 from Sasol) | |
| 2-Octyldodecan-1-ol | 5% |
| (Eutanol G from BASF) | |
| Oxypropylenated (14 OP) | 5% |
| butyl alcohol | |
| Aluminium hydroxychloride | 15% |
| as an aqueous 50% solution | |
| Isododecane | 20% |
| Polymer 1 as previously synthesized | 1% |
| Cyclohexasiloxane | 22% |

| Hair-conditioning mask | O |
|---|---|
| Cetylstearyl alcohol (50/50 C16/C18) | 5% |
| (Lanette O OR from BASF) | |
| Mixture of myristyl stearate | 5% |
| and myristyl palmitate (Myristyl | |
| myristate 1315 from Stearinerie Dubois) | |
| Behenyltrimethylammonium chloride | 4% |
| (Genamin KDMF from Clariant) | |
| Polymer 1 as previously synthesized | 1% |
| Undecane/tridecane | 3% |
| (Cetiol UT from BASF) | |
| Refined avocado oil | 5% |
| Hydroxyethylcellulose (MW: 1,300, 000) | 0.2% |
| (Natrosol 250 HHR from Ashland) | |
| Preserving agent(s) | 0.3% |
| Demineralized water | qs 100 |

| W/O Reverse emulsion | P |
|---|---|
| Oxyethylenated polymethylcetyldi- | 3% |
| methylmethylsiloxane (20/75/5- | |
| viscosity: 3000 cSt) (Abil EM | |
| 90 from Evonik Goldschmidt) | |
| Polyglycery-4 isostearate | 1% |
| (Isolan GI 34 from Evonik Goldschmidt) | |
| Mixture of mineral oil, | 3% |
| microcrystalline wax and paraffin | |
| (Vaseline Blanche Codex | |
| 236 from Aiglon) | |
| Polymer 1 as | 1% |
| previously synthesized | |
| Undecane/tridecane | 10% |
| (Cetiol UT from BASF) | |
| Silica | 3% |
| (Spherica P1500 from | |
| JGC Catalysts & Chemicals) | |

-continued

| W/O Reverse emulsion | P |
|---|---|
| Distearyldimethylammonium-modified hectorite (Bentone 38 VCG from Elementis) | 0.4% |
| Glycerol | 5% |
| Magnesium sulfate heptahydrate | 0.7% |
| Polydimethylsiloxane (viscosity: 10 cSt) (Element14 PDMS 10-A from Momentive Performance Materials) | 10% |
| Preserving agent(s) | 0.3% |
| Demineralized water | qs 100 |

| Fragranced wax | Q |
|---|---|
| Fragrance(s) | 5% |
| Polymer 1 as previously synthesized | 1% |
| Isododecane (Permethyl 99 A from Permethyl) | qs 100 |

The compositions described in the illustrative examples K, L, M, N, O, P and Q above, combining a lipophilic polymer as claimed (Polymer 1) and a volatile hydrocarbon (composition in accordance with the invention), are in the form of smooth homogeneous compositions, without any grain perceived during their application to the skin, they leave no greasy film, are easy to apply and are rapidly absorbed by the skin.

The invention claimed is:

1. A composition for topical application comprising at least one fatty phase; at least one volatile hydrocarbon-based oil chosen from hydrocarbon-based oils containing from 8 to 16 carbon atoms; and at least one lipophilic polymer comprising monomer units of formulae (A) and (B):

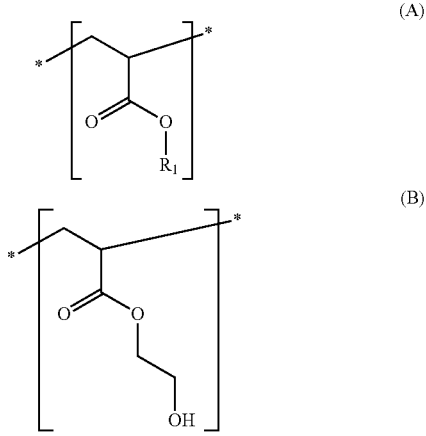

in which:
$R_1$, independently at each occurrence, is chosen from alkyl or alkylene radicals;
with at least 60% by weight of the groups $R_1$ being behenyl radicals, the weight percentage relating to the sum of all the groups $R_1$ present in the polymer;
the weight ratio of the sum of all the hydroxyethyl acrylate units to the sum of all the acrylate units bearing the group $R_1$ ranges from 1:30 to 1:1; and
the sum of all of the units A and B is at least 95% by weight relative to the total weight of the polymer;
the lipophilic polymer having a number-average molecular weight Mn ranging from 2000 to 9000 g/mol.

2. The composition according to claim 1, in which the at least one volatile hydrocarbon-based oil is liquid at room temperature and has a non-zero vapour pressure, at room temperature and atmospheric pressure.

3. The composition according to claim 1, in which the at least one volatile hydrocarbon-based oil is other than fragranced oils.

4. The composition according to claim 1, in which the at least one volatile hydrocarbon-based oil is other than terpenes.

5. The composition according to claim 1, in which the volatile hydrocarbon-based oil(s) are chosen from branched C8-C16 alkanes.

6. The composition according to claim 1, in which the at least one volatile hydrocarbon-based oil is chosen from isododecane, isodecane and isohexadecane, and mixtures thereof.

7. The composition according to claim 1, in which the at least one volatile hydrocarbon-based oil is chosen from volatile linear alkanes comprising from 8 to 16 carbon atoms.

8. The composition according to claim 1, in which the at least one volatile hydrocarbon-based oil is chosen from n-octane (C8), n-nonane (C9), n-decane (C10), n-undecane (C11), n-dodecane (C12), n-tridecane (C13), n-tetradecane (C14) and hexadecane (C16), and mixtures thereof.

9. The composition according to claim 1, in which the at least one volatile hydrocarbon-based oil is present in a content ranging from 0.1% to 90% by weight relative to the total weight of the composition.

10. The composition according to claim 1, in which the mass ratio between the at least one lipophilic polymer and the at least one volatile hydrocarbon-based oil is between 1:1 and 1:6.

11. The composition according to claim 1, comprising at least one solid fatty substance.

12. The composition according to claim 1, in which, in the at least one lipophilic polymer, $R_1$ consists of alkyl radicals.

13. The composition according to claim 1, in which, in the at least one lipophilic polymer, at least 70% by weight of the $R_1$ groups are behenyl radicals.

14. The composition according to claim 1, in which, in the at least one lipophilic polymer, all the groups $R_1$ are behenyl radicals.

15. The composition according to claim 1, in which, in the at least one lipophilic polymer, the weight ratio of the sum of all the hydroxyethyl acrylate units to the sum of all the acrylate units bearing the group $R_1$ ranges from 1:15 to 1:1.

16. The composition according to claim 1, in which the at least one lipophilic polymer has a number-average molecular weight Mn ranging from 5000 to 9000 g/mol.

17. The composition according to claim 1, in which the at least one lipophilic polymer has a melting point ranging from 60° C. to 69° C.

18. The composition according to claim 1, in which the at least one lipophilic polymer is present in an amount of active material ranging from 0.1% 10% by weight relative to the total weight of the composition.

19. The composition according to claim 1, comprising at least one aqueous phase.

20. A process for the cosmetic treatment of a keratin material, in which a composition as defined in claim 1 is applied to the keratin material.

21. A process for caring for, protecting and/or making up keratin materials which comprises applying a composition as defined in claim 1, to the keratin materials.

* * * * *